United States Patent [19]
Whitwam et al.

[11] Patent Number: 5,271,388
[45] Date of Patent: Dec. 21, 1993

[54] MEDICAL VENTILATOR

[75] Inventors: James G. Whitwam, London; Mihir K. Chakrabarti, Greenford, both of England

[73] Assignee: Caduceus Limited, London, England

[21] Appl. No.: 778,130

[22] PCT Filed: Jun. 5, 1990

[86] PCT No.: PCT/GB90/00871

§ 371 Date: Jan. 24, 1992

§ 102(e) Date: Jan. 24, 1992

[87] PCT Pub. No.: WO90/14853

PCT Pub. Date: Dec. 13, 1990

[30] Foreign Application Priority Data

Jun. 7, 1989 [GB] United Kingdom ............... 8913084

[51] Int. Cl.⁵ .................................................. A61M 16/00
[52] U.S. Cl. ........................... 128/204.18; 128/204.24; 128/204.25
[58] Field of Search ............. 128/204.18, 204.24, 128/204.25, 912, 205.24; 137/891, 892, 888

[56] References Cited

U.S. PATENT DOCUMENTS

| | | | |
|---|---|---|---|
| 1,214,941 | 2/1917 | Morris et al. | 128/204.25 |
| 3,485,243 | 12/1969 | Bird et al. | 128/204.25 |
| 3,741,208 | 6/1973 | Jonsson et al. | 128/204.21 |
| 3,961,627 | 6/1976 | Ernst et al. | 128/204.21 |
| 3,976,064 | 8/1976 | Wood et al. | 128/204.21 |
| 4,471,773 | 9/1984 | Bunnell et al. | 128/204.21 |
| 4,481,944 | 11/1984 | Bunnell | 128/204.18 |
| 4,495,946 | 1/1985 | Lemer | 128/204.25 |
| 4,520,812 | 6/1985 | Freitag et al. | 128/204.25 |
| 4,537,190 | 8/1985 | Caillot et al. | 128/204.22 |
| 4,596,247 | 6/1986 | Whitwam et al. | 128/204.25 |
| 4,957,107 | 9/1990 | Sipin | 128/204.21 |
| 4,971,049 | 11/1990 | Rotariu et al. | 128/204.21 |
| 5,107,830 | 4/1992 | Younes | 128/204.18 |

FOREIGN PATENT DOCUMENTS

| | | |
|---|---|---|
| 0082041 | 6/1983 | European Pat. Off. . |
| 0080155 | 11/1984 | European Pat. Off. . |
| 0234736 | 9/1987 | European Pat. Off. . |
| 309595 | 12/1918 | Fed. Rep. of Germany . |
| 2221152 | 10/1974 | France . |
| 2117648A | 10/1983 | United Kingdom . |
| 2137887 | 10/1984 | United Kingdom ........... 128/204.24 |

Primary Examiner—Edgar S. Burr
Assistant Examiner—Aaron J. Lewis
Attorney, Agent, or Firm—Klarquist, Sparkman, Campbell, Leigh & Whinston

[57] ABSTRACT

An oscillatory medical ventilator comprises a ventilator duct having one end for attachment to the a patient tube. A gas supply jet is mounted in a bearing block for rotation by an electric motor. The jet has a gas supply passage to which driving or respiratory gas is supplied continuously during rotation of the jet by a gas supply chamber encircling a shaft of the jet and communicating with the passage through radially extending openings in the wall of the shaft. A cyclically varying pressure at one end of the ventilator duct is thus produced upon rotation of the jet to cause alternating inflation and deflation of the lungs with respiratory gas which is supplied either by the jet or an independent source connected to the patient tube.

7 Claims, 2 Drawing Sheets

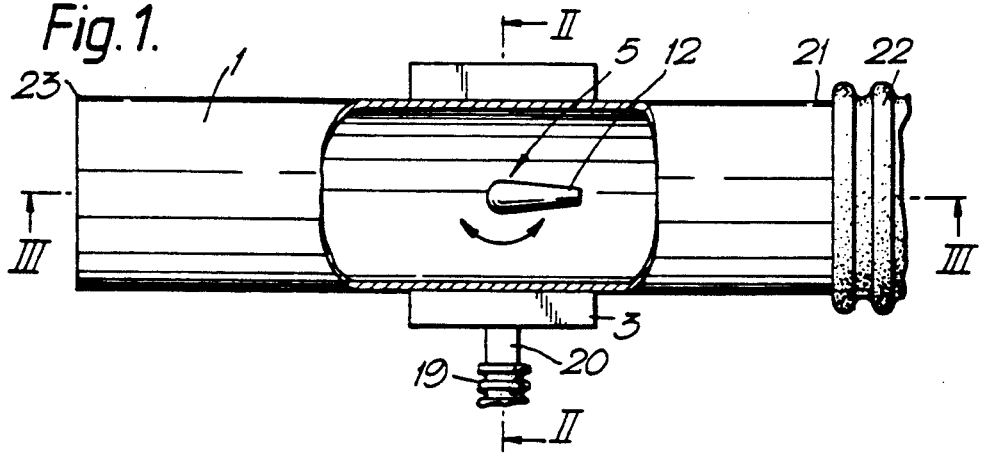
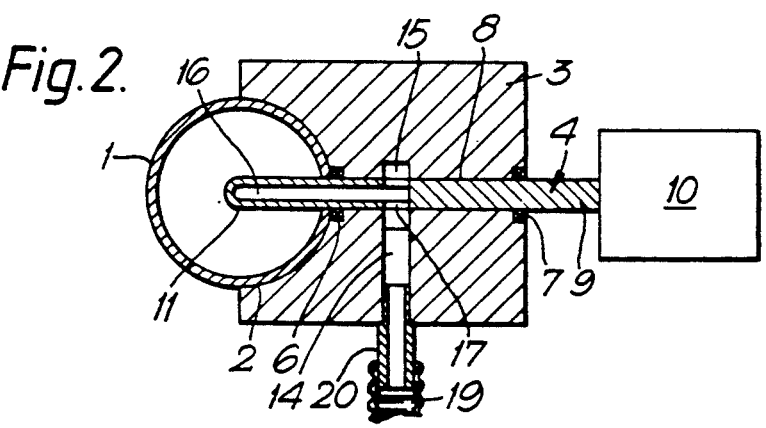
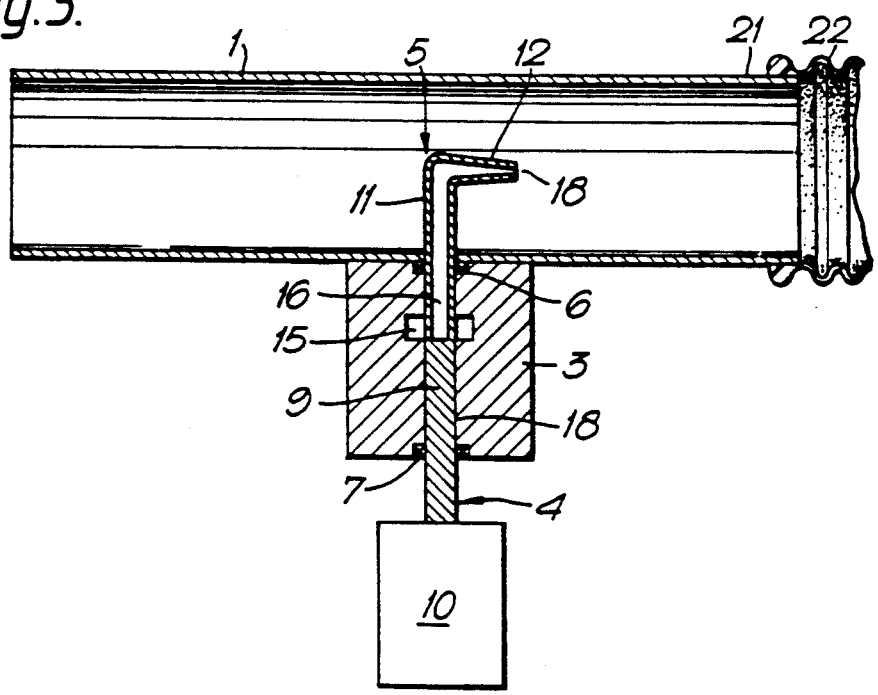

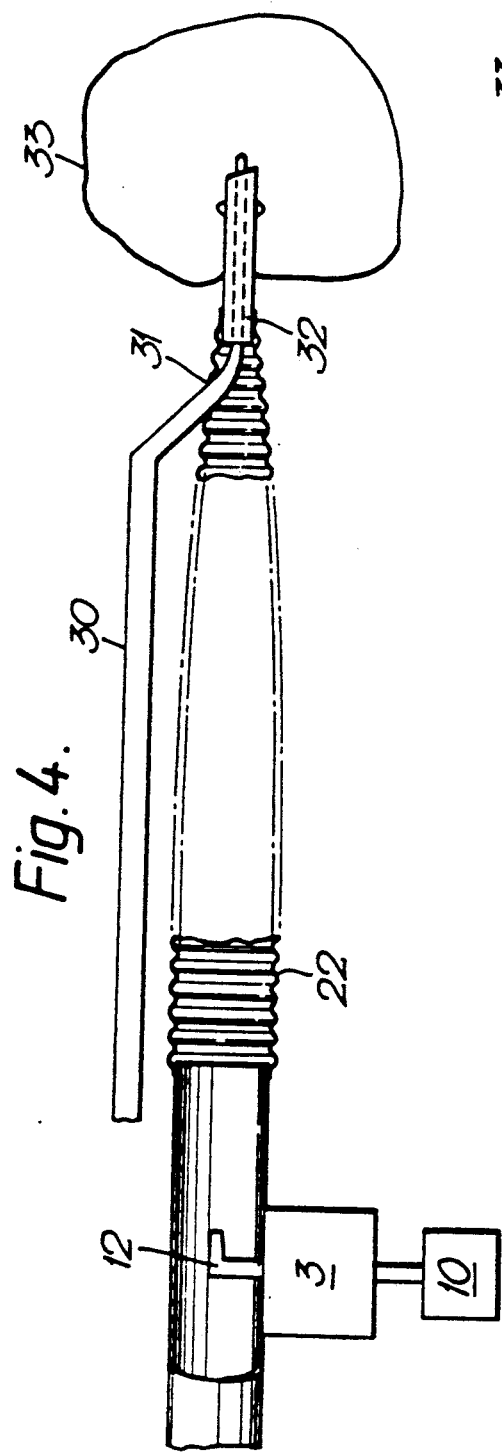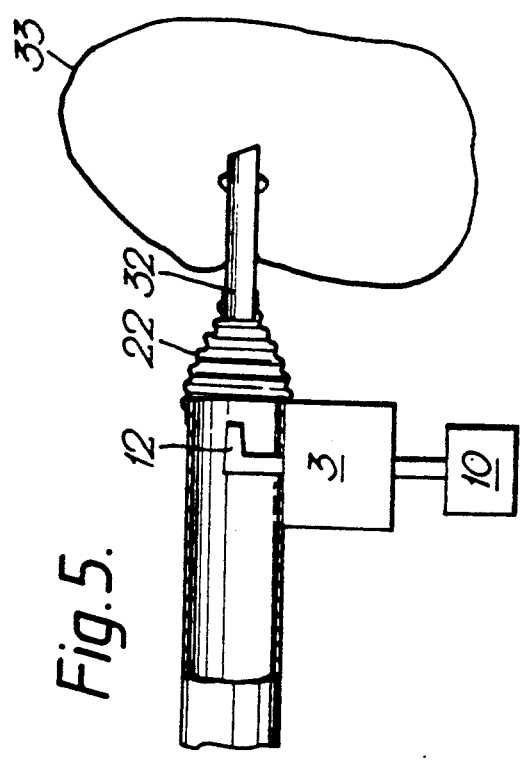

MEDICAL VENTILATOR

This invention relates to improvements in or relating to medical ventilators and, more particularly, to a medical ventilator which is especially, but not exclusively, useful for high frequency ventilation or oscillation of a patient.

Medical ventilators are extensively used in varying circumstances to replace or assist the natural breathing process of a patient in whom this function is impaired.

Under some circumstances and for particular purposes, it is advantageous to ventilate the lungs of a patient at breathing rates which are higher than spontaneous breathing rates with the aid of a high frequency medical ventilator which may provide breathing rates of up to 3000 breaths per minute (bpm).

A known high frequency medical ventilator or oscillator comprises a ventilator duct which has a patient end for attachment to a patient tube adapted to be introduced into the trachea of a patient whose breathing is to be sustained or augmented by the ventilator. Respiratory gas is introduced into the ventilator duct through two fixed jets extending into the ventilator duct, one of the jets having an outlet orifice facing the patient end of the ventilator duct and the other jet having its outlet orifice facing away from the patient end of the duct. Pulses of respiratory gas are fed alternatively to the two jets so that the patient tube is alternately subjected to high and low pressure, causing an alternating upstream and downstream flow of gas to and from the lungs of the patient in a cyclical way. Other high frequency ventilators are normally closed systems and employ either piston or bellows devices.

While these known high frequency medical ventilators function more or less satisfactorily under some conditions, either they are bulky or the pressure waveform resulting from the alternate pulsing of the two oppositely facing jets is not entirely satisfactory. Also, the synchronization of the pulsed gases supplied to the two jets to maintain the required lung (alveolar) expansion is critical and may be difficult to arrange safely in a clinical situation. The complexity in the breathing circuit of a closed system has made it unsafe and difficult for routine clinical use.

It is an object of the present invention to provide an improved medical oscillatory ventilator which finds particular application as a high frequency ventilator and, to this end, the invention provides a medical ventilator comprising a ventilator duct having a patient end for attachment to a patient tube ; a respiratory gas supply jet extending into the patient duct and mounted for rotation about an axis transverse to the axis of the ventilator duct, the jet having a gas supply passage terminating in an outlet orifice arranged to direct gas into the ventilator duct in a direction transverse to the axis of rotation of the jet; means for rotating the jet about the axis of rotation; and means for continuously supplying gas to the passage in the jet as the jet rotates to produce a cyclically varying flow of gas to and from the patient end of the ventilator duct.

In an embodiment of the ventilator a gas supply chamber encircles a rotatably mounted shaft of the jet and communicates with the gas supply passage in the jet through radially extending openings in the shaft of the jet.

Preferably, the shaft of the jet is rotatably mounted in a bearing block which is formed with a gas supply conduit extending transversely of the axis of rotation of the shaft of the jet and which terminates in the gas supply chamber.

The means for rotating the jet conveniently comprises an electric motor.

In order that the invention may be readily understood, embodiments thereof will now be described by way of example, with reference to the accompanying drawings, in which:

FIG. 1 is a side view of a medical ventilator embodying the present invention, partly sectioned to show a rotatable jet within the ventilator duct;

FIG. 2 is a cross-sectional view on the line II—II of FIG. 1, with an electric motor of the ventilator unsectioned;

FIG. 3 is a cross-sectional view on the line of FIG. 1 with the electric motor of the ventilator again unsectioned.

FIG. 4 is a diagrammatic view of one configuration in which a medical ventilator embodying the invention may be employed; and FIG. 5 is a diagrammatic view of another configuration in which a medical ventilator embodying the invention may be employed.

Referring now to the drawings, a medical ventilator embodying the present invention comprises a ventilator duct 1 seated and retained by suitable means (not shown) in a semi-cylindrical recess 2 of a mounting and bearing block 3.

A shaft portion 4 of a jet 5 is rotatably mounted by bearings 6 and 7 in a bore 8 of the mounting block which extends transversely of the axis of the ventilator duct 1. One end portion 9 of the shaft 4 projects from the bearing block 3 and is coupled to an electric motor 10 for rotating the shaft 4 about its axis. A portion 11 at the other end of the shaft 4 projects into the ventilator duct l through a corresponding aperture in the wall of the duct 1 and terminates in a nozzle 12 extending at right angles to the axis of rotation of the shaft 4.

The bearing block 3 is formed with a gas supply conduit 14 extending transversely of the bore 8 and communicating with an annular chamber 15 encircling the shaft 4 of the jet. The annular chamber 15 is maintained in constant communication with a passage 16 in the jet 5 by radial openings 17 in the jet. The passage 16 extends through the jet 5 from the openings 17 to an outlet orifice 18 of the nozzle 12.

Gas is supplied to the bearing block 3 by means of a flexible gas tube 19 coupled to the conduit 14 by a screw-threaded spigot 20. The source of the gas may be a piped supply or cylinder of pressurized air and/or oxygen at a pressure of 50 to 60 pounds per square inch (psi) and may deliver gas to the conduit 14 via a pressure reducing valve or other flow control means (not shown) providing a pressure or flow ranging from 0 to 60 psi or 0–200 /min respectively, or even higher.

The motor 10 is a variable speed motor capable of rotating the shaft 4 at any selected speed. For example, a speed range of 0 to 3000 revolutions per minute (rpm) or even higher may be suitable.

A patient end 21 of the ventilator duct 1 is connected to one end of a flexible patient tube 22 having its other end adapted to be connected to the airways (trachea) of a patient. The other end 23 of the ventilator duct 1 may be open or may be coupled to further equipment for treating the patient via the ventilator.

In use of the described oscillatory ventilator, gas is supplied continuously to the jet 5 at a selected pressure and the jet is simultaneously rotated a clockwise or anticlockwise direction (FIG. 1) at a selected speed corresponding to the required number of breaths per minute. The stream of gas emerging from the outlet orifice 18 of the jet 5 is thus swept around a circular path within the respirator duct 1, producing a substantially sinusoidal gas flow creating positive and negative pressure variation at the patient end 21 of the duct and thus a corresponding cyclical flow of gas to and from the patient at a frequency determined by the speed of rotation of the jet 5.

FIG. 4 illustrates one configuration in which the ventilator of FIGS. 1 to 3 may be employed. In the FIG. 4 arrangement, the gas delivered by the rotating jet 12 serves indirectly as a pneumatic piston to drive respiratory fresh gas which is supplied through a separate relatively narrow supply duct 30 at a steady relatively low pressure and flow rate to an inlet 31 of a detachable tracheal tube 32 which terminates the patient tube 22 and which is inserted in the airway of the patient 33. In this configuration the distance between the rotating jet and the inlet 31 is such that the gas supplied to the rotating jet acts purely to generate a driving force for the respiratory fresh gas, the column of gas in the tubes 21, 22 between the jet and the fresh gas inlet acting as a pneumatic piston through which the sinusoidal pressure variation generated by the gas leaving the jet is transmitted to the respiratory fresh gas at the inlet of the tracheal tube. Clearly, in this configuration the gas supplied to the rotating jet 12 does not itself need to be respiratory gas. Exhaled gas from the patient passes into the relatively wide patient tube beyond the fresh gas inlet during the low pressure phases of the driving pressure so that it is not inspired during the following high pressure phase. It is envisaged that, instead of terminating at inlet 31, the duct 30 could be extended through the tube 32 to deliver fresh gas directly into the patient's airways as indicated by the extension 34 shown in dashed lines in FIG. 4.

FIG. 5 illustrates another configuration in which the ventilator of FIGS. 1 to 3 may be employed. In the FIG. 5 arrangement, the patient end of the ventilator duct is connected to the tracheal tube 32 by a very short patient tube 22, so that the rotating jet 12 is disposed closely adjacent to the tracheal tube 32, and the jet 12 is supplied with respiratory fresh gas for ventilation of the lungs by the gas from the jet. In this configuration, the respiratory fresh gas from the jet 12 is delivered at varying sinusoidal pressure directly into the tracheal tube 32. Exhaled gas from the patient passes through the relatively wide patient tube beyond the jet 12 and takes no part in the next inspiration phase.

It is envisaged that the above described oscillatory medical ventilator will find application in diverse circumstances where the use of a ventilator is required. Examples of likely uses are for: total ventilation of patients at low and normal frequencies of ventilation and high frequency ventilation or oscillation up to 3000 bpm or above; the superimposition of oscillation on any other system being used for ventilation, whether normal or high frequency; and to assist spontaneous ventilation.

We claim:

1. A medical ventilator, comprising:
    a ventilator duct having one end for attachment to a patient tube and another end;
    a gas supply jet extending into the ventilator duct and mounted for rotation about an axis transverse to the axis of the duct extending between said end, the jet having a gas supply passage terminating in an outlet orifice arranged to direct gas into the ventilator duct in a direction transverse to the axis of rotation of the jet;
    a gas source for continuously supplying gas to the passage in the jet; and
    a motor for continuously rotating the jet about the axis of rotation at a speed corresponding to the required breathing rate so as to produce a substantially sinusoidal gas flow creating cyclical positive and negative pressure variation at the one end of the ventilator duct and thus a corresponding cyclical flow of gas to and from the patient at a frequency determined by the speed of rotation of the jet.

2. A ventilator according to claim 1, wherein a gas supplying chamber encircles a rotatably mounted shaft of the jet and communicates with the gas supply passage in the jet through radially extending openings in the shaft of the jet.

3. A ventilator according to claim 2, wherein the shaft of the jet is rotatably mounted in a bearing block which is formed with a gas supply conduit extending transversely of the axis of rotation of the shaft of the jet and which terminates in the gas supply chamber.

4. A ventilator according to claims 1, 2, or 3, wherein the motor for rotating the jet comprises and electric motor.

5. A medical ventilator arrangement, comprising a ventilator according to claim 1, 2, or 3, wherein the ventilator is connected to a patient tube having a respiratory fresh gas inlet for connection to a respiratory fresh ga supply delivering respiratory fresh gas at a steady pressure, the distance between the rotatable jet and the respiratory fresh gas inlet being such that driving gas delivered by the jet acts to impose the cyclically varying pressure on respiratory fresh gas supply to the respiratory fresh gas inlet.

6. A medical ventilator arrangement, comprising a ventilator according to claim 1, 2, or 3, wherein the ventilator is connected to a patient tube, the rotatable jet being positioned adjacent to the gas inlet of the patient tube and being supplied with respiratory fresh gas which is delivered at the cyclically varying pressure to the respiratory gas inlet.

7. A method of operating a medical ventilator, comprising the steps of:
    providing a ventilator duct having one end for attachment to a patient tube and another end;
    providing a gas supply jet extending into the ventilator duct and mounted for rotation about an axis transverse to the axis of the duct extending between said ends, the jet having a gas supply passage terminating in an outlet orifice arranged to direct gas into the ventilator duct in a direction transverse to the axis of rotation of the jet;
    providing a gas source for continuously supplying gas to the passage in the jet;
    continuously supplying gas to the gas supply jet;
    providing a motor; and
    continuously rotating the jet at a selected speed corresponding to the required breathing rate, with the rotation producing a substantially sinusoidal gas flow creating cyclical positive and negative pressure variation at the one end of the ventilator duct which results in a corresponding cyclical flow of gas to and from the patient at a frequency determine by the speed of rotation of the jet.

* * * * *